United States Patent [19]

Inagaki

[11] Patent Number: 5,055,152
[45] Date of Patent: Oct. 8, 1991

[54] EASILY SEPARABLE LAMINATED/PERFORATED FILM FOR PACKINGS, AND ITS MANUFACTURING METHOD

[75] Inventor: Hiromichi Inagaki, Inuyama, Japan

[73] Assignees: Mitsubishi Monsanto Chemical Company; Nihon Tokkyo Kanri Company Limited, both of Tokyo, Japan

[21] Appl. No.: 443,706

[22] Filed: Nov. 29, 1989

[30] Foreign Application Priority Data

Nov. 30, 1988 [JP] Japan ................................ 63-304624
Dec. 10, 1988 [JP] Japan ................................ 63-312361

[51] Int. Cl.$^5$ ........................ B29C 47/00; B32B 31/18
[52] U.S. Cl. ........................ 156/244.11; 156/244.18; 156/244.27; 156/252; 156/253
[58] Field of Search ................ 156/244.11, 244.18, 156/244.24, 252, 253, 244.27

[56] References Cited

U.S. PATENT DOCUMENTS

| | | | |
|---|---|---|---|
| 2,688,581 | 9/1954 | Stubbs | 156/252 |
| 3,393,118 | 7/1968 | Ekström | 156/252 |
| 3,410,395 | 11/1968 | Sellers | 156/252 |
| 3,553,067 | 1/1971 | Dwyer et al. | 156/252 |
| 4,636,273 | 1/1989 | Wolfersperger | 156/252 |

*Primary Examiner*—Caleb Weston
*Attorney, Agent, or Firm*—McGlew & Tuttle

[57] ABSTRACT

The present invention relates to an easily separable laminated/perforated film for packings, that can seal the contents under transportation and storage situations and can be formed to the situation for communicating the container interior with the external side when it is to be used.

This laminated/perforated film is the film which has bonded both the films in simulation by providing many perforations onto a formed film and by pressing another film which has been extruded from a film forming machine and which is still in a fused state against this perforated film, and this simulation bonding is to be achieved when the film in the fused state has invaded into the perforations of another film.

4 Claims, 5 Drawing Sheets

EASILY SEPARABLE LAMINATED/PERFORATED FILM FOR PACKINGS, AND ITS MANUFACTURING METHOD

FIELD OF THE INVENTION

This invention relates to an easily separable laminated/perforated film for packings, which is made of the plastic being produced with its objects being to be used for the packing of foodstuffs and for the packing of drugs.

DESCRIPTION OF THE PRIOR ART

In the case of the foodstuffs, drugs, etc., the material is sealed into the containers under the transportation and storage situations. Unless a part or the entirety of the container should be opened for its formation into the state for communicating the packing container interior with the external side when heating up or steaming the entirety of container in an electronic range or the like to each the contents, the packing container is destined to be ruptured because of its internal pressure.

Therefore, when heating up or cooking a foodstuff, conventionally the foodstuff needs to be shifted from the packing container interior on each cooking occasion, or a part of the packing container needs to be opened by using a pair of scissors.

Further, such drugs as coated drugs, pasted drugs, wet cloth drugs and adhesive plaster need to be matched to skins by opening the packing container when being used, but in the case of these types of drugs, a bonding agent has been kneaded into them together with the drugs for the purpose of providing an adhesion, and the quantity of bonding agent is larger than that of drug, which poses a problem especially to the drug efficacy and durability. In addition, if the quantity of drug should be increased for providing the drug efficacy and durability, the drug itself is enlarged in size which is not simply inferior in outward appearance as a pasted drug but whose price becomes high. Moreover, such drugs as drying agents, moth-proofing agents, and deoxydating agents are first packed into individual packs having a ventilation property, which are further packed, for example, in 5 pcs or 10 pcs, into a large external packing bag having an airtightness property, and these small packs are taken one by one out of the large external bag by opening it when they are to be used. However, this type of packing pattern requires double packings, which is troublesome and moreover, if the external bag should once be opened, the residual small packs come in contact with the air, thereby the drug efficacy and durability tend to be lost.

OBJECTS OF THE INVENTION

An object of this invention is to provide a laminated/perforated film and its manufacturing method that can be laid on a packing machine as a sheet of film when packing such contents as foodstuffs and the like and enables air and liquid to pass through the perforations of this film or allows a drug to come into contact directly with skin while getting separated easily and leaving over a sheet of film with many perforations provided thereon during its usage.

Another object of this invention is to present the means for enhancing the separation strength without using a bonding agent in the aforementioned laminated/perforated film for packings.

DETAILED DESCRIPTION

Figure 1:
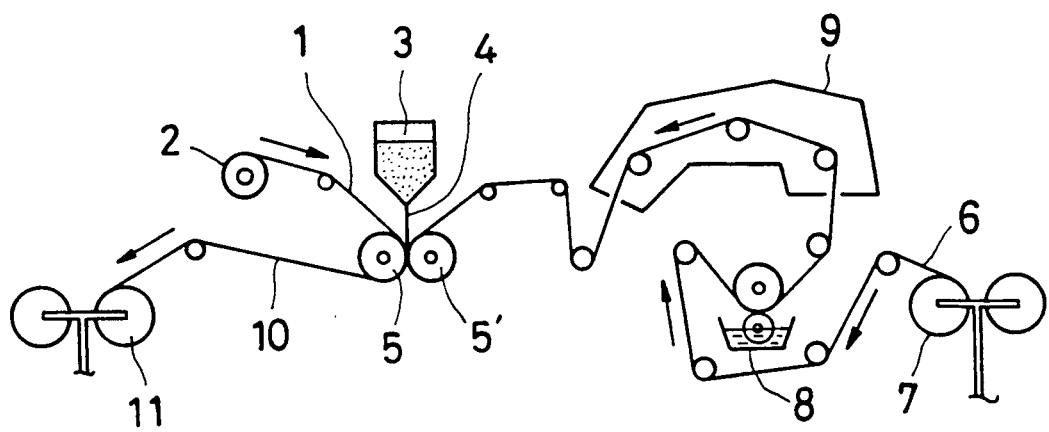
FIG. 1 is an explanatory view of the manufacturing method of the laminated/perforated film relating to this invention.

The manufacturing method of the laminated/perforated film relating to this invention is shown in FIG. 1.

A perforated film 1 has been rolled up around a roller 2, and the perforated film being fed out of this roller 2 is a molded polypropylene film through which many 0.6 mm holes are perforated uniformly at a 2 mm pitch interval, and a polyethylene and the like can be utilized as the raw material of this perforated film.

Element 3 is a fusion extruder, and the fused polyethylene is extruded from this fusion extruder and is pressed against the aforesaid perforated film 1 in the state of having maintained this fused state by rollers 5 and 5'.

Figure 2:
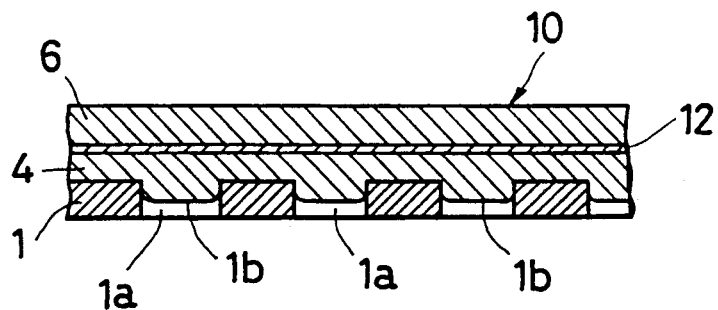
FIG. 2 is a sectional view of the laminated/perforated film for packings.

FIG. 2 is a sectional view in the state of having pressed the fused polyethylene into the formation of a sheet of laminated film, and the film 4 in the fused state gets into the perforations 1a of perforated film 1 when it is pressed between the roller 5 and 5'. These sinking portions 1b uniformly get into all the perforations 1a of perforated film 2. However, both the elements don't get fused to each other, which is an apparent bonding and is a simulated bonding.

Element 6 is a polyester film which becomes a basic material film, and this material which has been formed into a film and rolled up around a roller 7 reaches the space between the rollers 5 and 5' passing through a bonding agent coating roller 8 and a drier 9, and is pasted up with the outside of aforesaid film 4.

The packing body 10 which has been manufactured in this way is rolled up in a rolling machine 11. The element 12 denoted in FIG. 2 is the bonding agent coated by the said bonding roller 8, where a polyethylene film 4 and a polyester film 6 are pasted up to each other.

Figure 3:
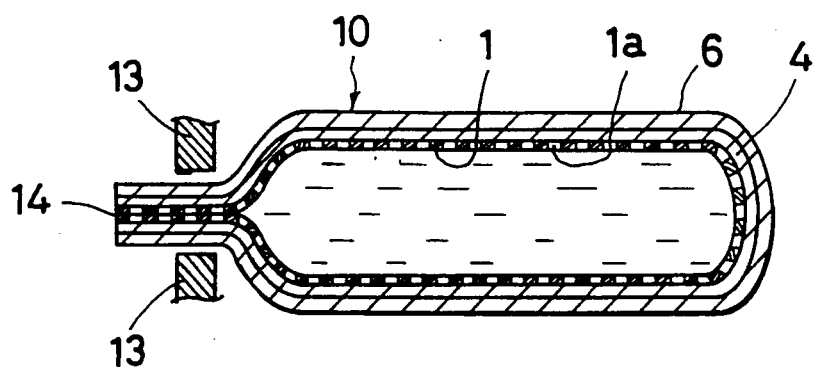
FIG. 3 is a sectional view in the state of having sealed a liquid using the film relating to the present invention.
Figure 4:
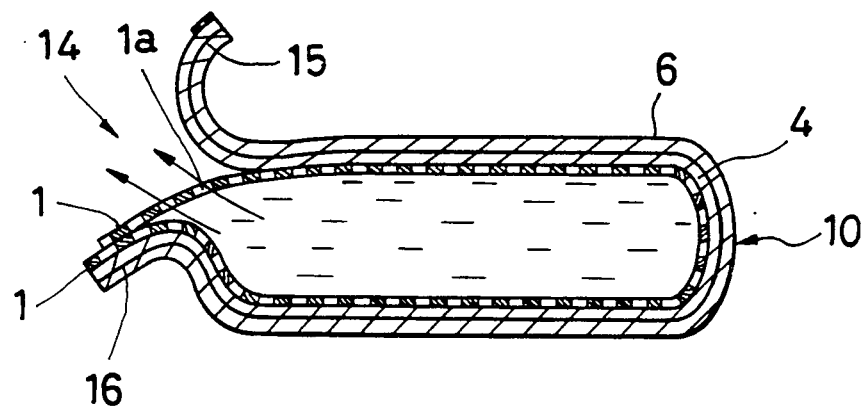
FIG. 4 is a sectional view in the state of having separated a part of the laminated film and having perforated the inner side film.

FIG. 3 shows the state of having sealed and packed a sauce using the aforesaid packing body, and the packing body 10 is heat-sealed by a heat seal bar 13. FIG. 4 shows an open state, and when the front side and rear side films are peeled away from each other in the open mouth 14, the perforated film 1 gets separated from the polyethylene film 4 on the side of the front 15 which has previously been processed to a weaker strength because of the simulated bonding, and moreover the perforated films 1 maintain the sealed state because they are heat-sealed mutually to each other. However, the sauce contained in the interior flows out of the perforations 1a of perforated film 1 when the bag is pressed with fingers or the bag is inclined. For this reason, because the sauce is not in the state for it to overflow at once, even such a liquid as sauce can be packed into a bag without any problem. Also, in the case of the foodstuff being heated up in an electronic range, microwave or the like, the bag can be opened as described above for venting air out of the perforations 1a of perforated film 1, and such a conventional problem can be eliminated as the foodstuff must be taken out of the bag, put into a container and must then be heated up.

Figure 5:
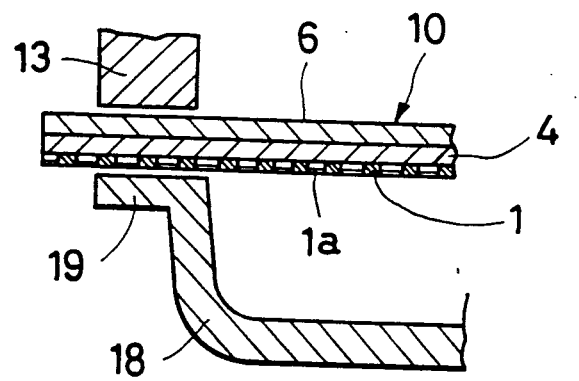
FIG. 5 is a sectional view indicating an embodiment of using the film according to this invention as the lid of a tray.
Figure 6:
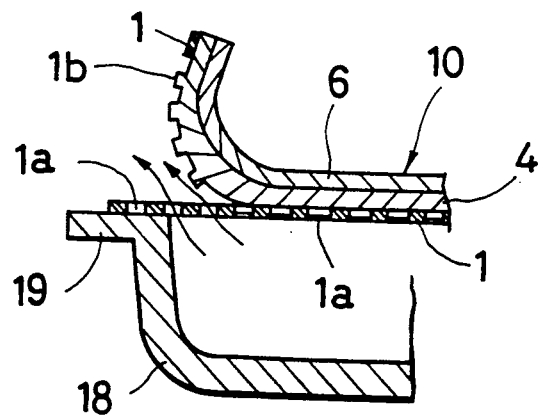
FIG. 6 is a sectional view in the state of having separated a part of laminated film in the lid of a tray.
Figure 7:
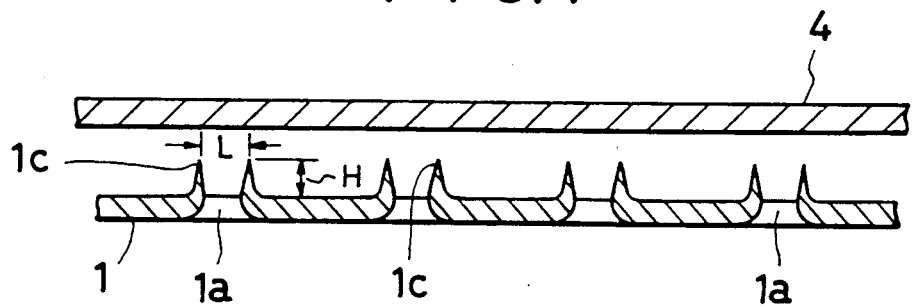
FIG. 7 is a sectional view showing an embodiment in the state of having formed this small perforation into a crater profile in perforating this film.
Figure 8:
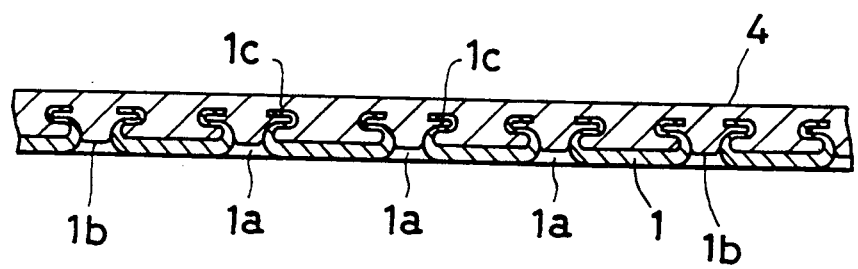
FIG. 8 is a sectional view of the film in the state of being laminated.

FIG. 5 and FIG. 6 show an example of using the packing body 10 relating to this invention as the lid of a container, where the packing body 10 is heat-sealed onto the edge 19 of a container 18 as illustrated in FIG. 5. When the film has separated as shown in FIG. 6, the perforated film 1 remains on the side of container 18 where the polyethylene film 4 and polyester film 6 sides alone get separated and the perforated film 1 keeps the container 18 sealed. For this reason, in the case of the foodstuff which needs to be cut from water, water can be cut easily from the perforations 1a without wetting your hands while keeping it contained inside the container 18.

FIG. 7 through FIG. 10 are the embodiments in the case of increasing the laminated strength, where the perforations 1a of perforated film 1 presents the crater profiles, and the fused state film 4 is to be pressed against the side of this crater profile for its pasting up. With this state formed in this way, the rib 1c of crater shape gets into the film 4, and the simulated bonding strength is heightened.

For reference, as the means for forming the perforated film 1 having the perforations 1c of aforesaid crater profiles, the method of pressing the polyethylene film against the roller having many vacuum perforations on one face of said material to suck up the polyethylene film into the said vacuum perforations for opening the perforations at the stage where this material, for example, a polyethylene film is still in the fused state. In addition, such a method of opening the perforations by sticking a needle shape perforating tool from one face is also imagined. However, any of these methods is premised upon the conditions that the mouth brim 1c of crater profile can be protrusively formed, and moreover upon the conditions that the size of diameter can also be adjusted optionally. Therefore, the abovementioned vacuum method is optimum as the technique capable of achieving these conditions easily.

The height of mouth brim 1c can be adjusted by the fused state of film. For example, if the fusion degree of film is high, the height of mouth brim 1c becomes greater and if the fusion degree is low, the said height becomes lower. This changes also depending on the nature of plastics, so this needs to be known empirically regarding the respective films. This also changes delicately even depending on the working environments (room temperature) of perforated film 1.

The quality of film 4 to be pasted up to the perforated film 1 is optional, but the fused state of film 4 when pressing it against the perforated plastic film 1 is such that the mouth brim 1c on the side of perforated plastic film gets into the thick wall portion and moreover needs to get deformed by the said pressing, so the state immediately after the formed film which has been extruded from a die is optimum.

Hereunder, the embodiment is to be explained in details.

Figure 9:
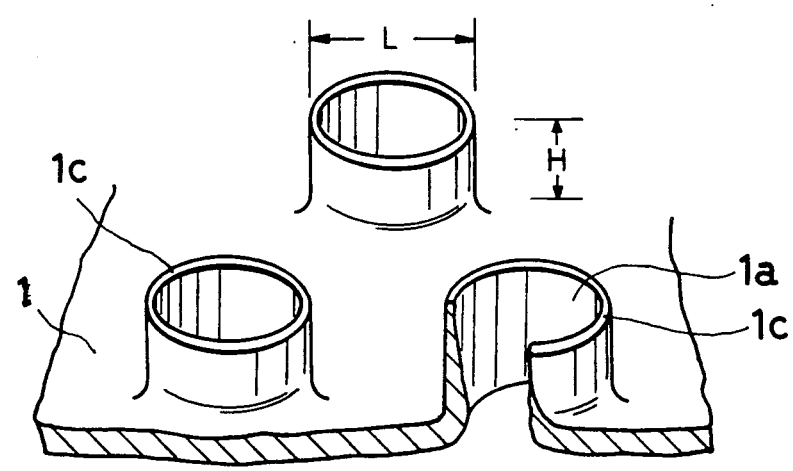
FIG. 9 is an explanatory view of perforations in crater profiles.
Figure 10:
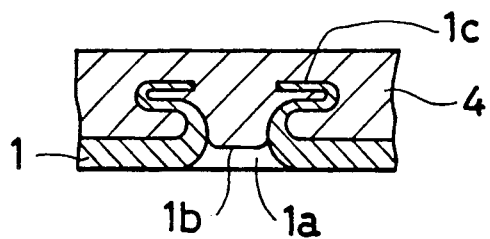
FIG. 10 is a laminated state explanatory sectional view in the perforations of crater profiles.

The perforated film 1 where the perforations 1a equipped with the mouth brim 1c of crater profile being formed on the polyethylene resin film by the vacuum system and the film 4 consisting of the polypropylene resin film in the fused state immediately after the extruded film are opposed to each other, which shall then be caught between the pressing rollers for its pressing to make the mouth brim 1c of perforations 1a got into the thick wall portion of film 4 and moreover to collapse it for its deformation. This state is illustrated in FIG. 10. FIG. 9 is an expanded view of perforations 1a in the perforated plastic film, and the diameter L and height H of mouth brim 1c in these perforations 1a are set up when forming these perforations 1a by the vacuum method. For enhancing the simulated bonding strength, it is enough to enlarge the diameter L and the height H and also to increase the number of perforations 1a. However, the strength can be heightened by increasing the H or L or the number of perforations out of these 3 conditions, and this can be determined by the problem of ventilation volume or by the problem of penetration into the interior, for example, when the film has been perforated.

Figure 11:
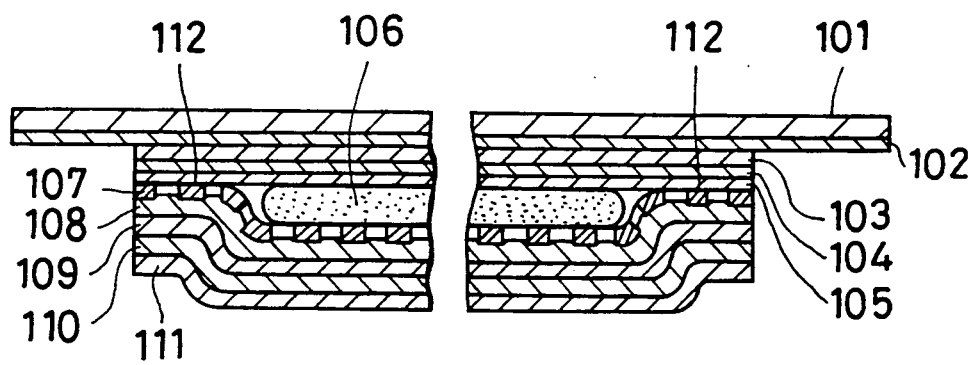
FIG. 11 is a sectional view in the state of having packed a percutaneous absorption drug using the film relating to this invention.
Figure 12:
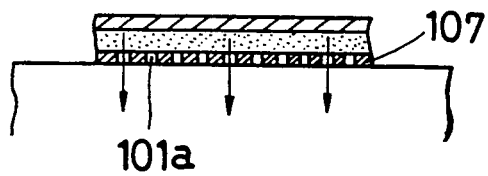
FIG. 12 is a sectional view in the state of having pasted a percutaneous absorption drug onto skin.
Figure 13:
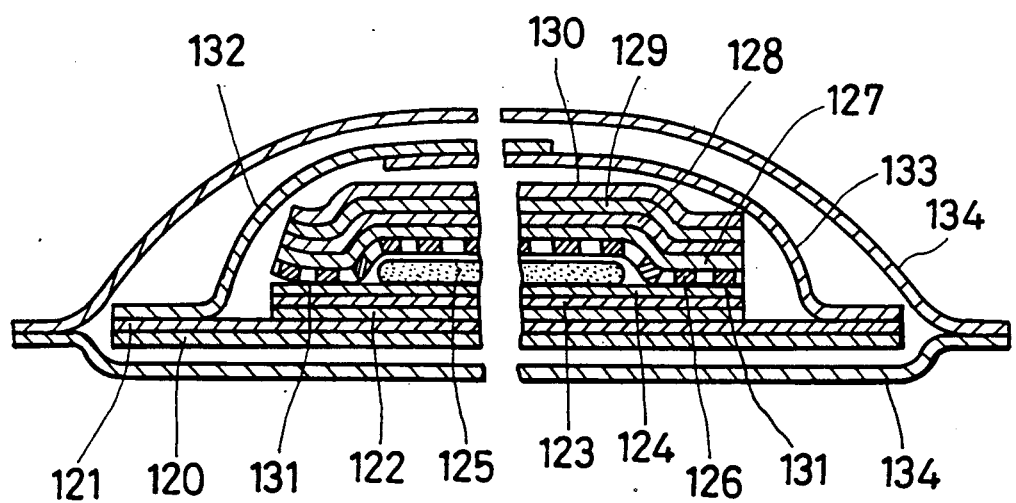
FIG. 13 is a sectional view of the adhesive plaster to which the film relating to the present invention has been utilized.

The examples of using the film relating to this inventions to the packing of drug are shown in FIG. 11 through FIG. 13.

In FIG. 11, element 101 is a pasting material consisting of a soft vinyl chloride, and a bonding agent layer 102 to be stuck directly onto a physical body is formed on this surface. Element 103 is a nylon film sticked onto the center of the surface of bonding agent layer 102, element 104 is an aluminium film pasted up onto the surface of this nylon film, and element 105 is a polyethylene film pasted up onto this surface.

Element 106 is the drug in a of paste state, element 107 is a perforated film where the perforations of 0.5 mm diameter are provided at 1 mm pitch onto a polyethylene film, while element 108 is a polypropylene film which has been bonded in simulation to the outside of this perforated film 107.

The means of simulation bonding is for making the fused film get into the perforations by forcedly pasting up the fused polypropylene film 108 under the film forming process onto the face of perforated film 107 by use of the rollers, and element 109 is an extended polypropylene film while element 110 is an aluminium film and element 111 is a nylon film, where the polypropylene film 108 through the nylon film 111 have been laminated into one body. However, since the perforated film 107 has also been bonded in simulation, it is one body in its outward appearance, and such processings as bag making, heat-sealing, etc. are carried out as one sheet of film.

Element 112 is the heat-sealed portion which has been executed around this area for sealing the aforesaid drug 106, where the perforated film 107 and the ethylene film 105 have been fused to each other.

FIG. 12 shows the usage example of the film pasted up onto a physical body, and when the area in and after the polypropylene film 108 which has been bonded in simulation is peeled away with the tips of fingers, this film can be broken away easily from the perforated film 107, and the drug 106 is covered by the perforated film 107 under this situation.

The drug 106 in the interior oozes out to the surface through the perforations 101a of perforated film 107, providing the drug efficacy.

FIG. 13 shows an embodiment of having applied the present invention to the adhesive plaster coated with drug, wherein element 120 is a soft vinyl chloride film, element 121 is a bonding agent layer on this surface, element 122 is a nylon film, element 123 is an aluminium film, element 124 is a polyethylene film, element 125 is a drug, element 126 is a perforated film, element 127 is a polypropylene film which has been bonded in simulation onto the said perforated film, element 129 is an aluminium film, element 130 is a nylon film and the polypropylene film 128 through the nylon film 130 are composed into one body.

Element 131 is the heat-sealed portion of polyethylene film 124 and perforated film 126, and the drug 125 in the interior has been sealed by this heat-sealed portion.

Elements 132 and 133 are the cover papers to cover the external side of said drug 125, and element 134 is an exterior.

In the case of the adhesive plaster having the construction in this way, the bonded portion in simulation with the perforated film 126 shall be peeled away by opening the exterior 134, breaking away the cover papers 132 and 133 and moreover by picking up the portion of polypropylene film 128.

This shall be used as an adhesive plaster by pasting up the bonding agent layer 121 onto a physical body similarly to the case of the embodiment which has been described above.

As mentioned above, the present invention has pressed the fused state film against the perforated film to make the fused state film get into the perforations provided on the perforated film, thereby achieving the simulated bonding.

As a result, because not simply the productivity is enhanced but its outward appearance is a sheet of film, this film can be handled as a sheet of film even if this film is to be used as a bag making or lid material. Consequently, the double processings required conventionally for the interior and the exterior become unnecessary.

Next, the simulated bonding strength can be selected by forming the mouth brims onto the perforations of perforated film and setting up their height and quantity optionally.

Moreover, by applying the film relating to this invention to such chemicals as pasted drug, its efficacy can be enhanced and moreover its durability or duration of potency can be elongated.

I claim:

1. A method for forming an easily separable laminated/perforated film, comprising the steps of:
   providing a plastic film in a fused state;
   providing a plastic perforated film said perforated film including brim portions protruding to form crater profiles with a protrusive mouth brim on one side of said perforated film, pressing said fused state plastic film against said perforated film on the protrusive mouth brim side and deforming the mouth brims within the fused state plastic film.

2. The method according to claim 1, wherein said fused state is formed by providing said plastic film immediately after said plastic film has been extruded from a fusion extruder.

3. Method according to claim 1 wherein a simulated bonding strength provided by pressing said films may be optionally adjusted by selecting a height, diameter and quantity of said mouth brims.

4. A method of forming an easily separable laminated-perforated film comprising the steps of:
   perforating a plastic film to form brim portions protruding to form crater profiles with protrusive mouth brims extending substantially parallel to a plane of the plastic perforated film;
   feeding the perforated film to a roller pair and feeding another plastic film to said roller pair and extruding plastic film from a fusion extruder and pressing the plastic film, in its fused state, between said plastic perforated film and said another plastic film and deforming said mouth brims to extend into said fused state plastic film.

* * * * *